United States Patent [19]

Pougalan et al.

[11] Patent Number: 4,734,278
[45] Date of Patent: Mar. 29, 1988

[54] PERFUMED POLYMERIC RESIN ESSENTIALLY CONSISTING OF A POLYETHER-ESTERAMIDE

[75] Inventors: Marc F. Pougalan, Noisiel, France; Günter Holzner, Grand-Lancy, Switzerland

[73] Assignee: Firmenich S.A., Geneva, Switzerland

[21] Appl. No.: 845,103

[22] Filed: Mar. 27, 1986

[30] Foreign Application Priority Data

Apr. 4, 1985 [CH] Switzerland ................... 1483/85

[51] Int. Cl.$^4$ ............... H61K 39/00; A01N 25/00; A01N 25/26
[52] U.S. Cl. ............................ 424/76.3; 424/409; 424/85; 424/76.4; 424/84; 523/102; 512/4
[58] Field of Search ............... 525/420, 408; 424/76, 424/78, 409, 85; 523/102; 252/522 A

[56] References Cited

U.S. PATENT DOCUMENTS

| 3,303,046 | 2/1967 | Chebiniak et al. | 117/36.1 |
| 3,594,342 | 7/1971 | Ratzsch et al. | 260/28.5 |
| 3,926,655 | 12/1975 | Miles | 106/243 |
| 4,184,099 | 1/1980 | Lindauer et al. | 424/78 |
| 4,208,493 | 6/1980 | Deleens et al. | 525/420 |
| 4,345,652 | 8/1982 | Mumcu | 525/420 |
| 4,464,456 | 8/1984 | Fiyikawa et al. | 522/18 |
| 4,590,111 | 5/1986 | Takeuchi | 428/475.2 |

FOREIGN PATENT DOCUMENTS

| 0023956 | 11/1980 | Fed. Rep. of Germany | 525/420 |
| 1176992 | 4/1959 | France | |
| 1201286 | 12/1959 | France | |
| 2273021 | 12/1975 | France | |

Primary Examiner—Joseph L. Schofer
Assistant Examiner—Peter F. Kulkosky
Attorney, Agent, or Firm—Pennie & Edmonds

[57] ABSTRACT

Shaped volatiles emitting body consisting essentially of a thermoplastic polyamidic resin of polyether-esteramide type of formula

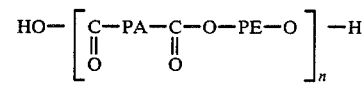

wherein PA represents the polyamide moiety and PE represents the polyether moiety, index n stands for an integer designating the multiple of the recurrent pattern, containing about 1 to 60% by weight, based on the total weight of the polyamidic resin, of a volatile substance selected from a perfume, an odorizer, a deodorizer, an insecticide, an insect- or an animal-repellent or attractant.

Article comprising a shaped volatiles emitting body substantially as described above.

6 Claims, No Drawings

PERFUMED POLYMERIC RESIN ESSENTIALLY CONSISTING OF A POLYETHER-ESTERAMIDE

BRIEF SUMMARY OF THE INVENTION

The present invention provides a shaped volatiles emitting body consisting essentially of a thermoplastic polyamidic resin of polyether-ester-amide type of formula

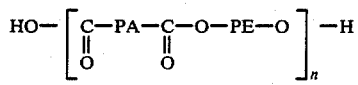

wherein PA represents the polyamide moiety and PE represents the polyether moiety, index n stands for an integer designating the multiple of the recurrent pattern, containing about 1 to 60% by weight, based on the total weight of the polyamidic resin, of a volatile substance selected from a perfume, an odorizer, a deodorizer, an insecticide, an insect- or an animal-repellent or attractant.

This invention more particularly provides a shaped volatiles emitting body wherein the polyether-ester-amide resin is obtained by reaction in the melting phase between a dicarboxylic polyamide having terminal carboxylic functions of a mean molecular weight of between about 300 and 15,000 and a linear or branched aliphatic polyoxyalkylene glycol having terminal hydroxylic functions and a mean molecular weight of between about 200 and 6,000, said reaction being carried out under substantial reduced pressure and at temperatures of between about 100° and 400° C. in the presence of a catalyst consisting of a tetraalkyl-orthotitanate of general formula Ti(OR)$_4$, wherein R represents a linear or branched aliphatic hydrocarbon radical having a number of carbon atoms of between 1 and 24 and wherein its weight proportion with respect to the reaction mixture is of between 0.01 and 5%.

This invention relates also to an article destined to odorize or deodorize ambient air or closed spaces, which article comprises substantially the shaped volatiles emitting body described above.

This invention relates further to an article destined to repel, attract or kill insects, which article comprises substantially the shaped volatiles emitting body described above.

BACKGROUND OF THE INVENTION

French Pat. No. 1,176,992, published on Apr. 17, 1959, describes a process for the preparation of "solid perfumes", process which consists in the bulky incorporation of a perfume in a synthetic resin. No specific resin however have been mentioned in the cited French patent.

U.S. Pat. No. 3,303,046, granted on Feb. 7, 1967, describes a process for the manufacture of porous compressible plastic materials and suggests the addition to the resulting products of various active ingredients such as pharmaceuticals, deodorants, perfumes or waxes.

Different polyamidic resins have been proposed in the past as gellifying agents. Their use was suggested at small concentrations in large solvent volumes and the resulting dispersions were employed as bases for the preparation of transparent lipsticks or for the manufacture of perfumed candles.

U.S. Pat. No. 3,926,655, granted to HERCULES Inc. on Dec. 16, 1975, discloses a material essentially solvent free consisting of a polyamidic resin containing a perfume oil. By means of the mentioned material, it was possible to manufacture perfumed articles of various forms and good transparency. In general, the polyamidic resins which present the most appropriate features for such a manufacture are those which derive from the condensation of polyamines, especially diamines and triamines, with dibasic acids of relatively high molecular weight, for example the acids derived from the dimerization of diunsaturated carboxylic acids. For instance, the above mentioned U.S. patent describes the condensation product between dimeric linoleic acid and ethylene diamine, which product possesses a molecular weight of between about 6,000 and 9,000. These polymeric products are commercially available under the name of VERSAMID (registered trademark of GENERAL MILLS, Inc.).

U.S. Pat. No. 4,184,099, granted to INTERNATIONAL FLAVORS & FRAGRANCES, Inc. on Jan. 15, 1980, discloses articles destined to deliver volatile substances such as perfumes, insecticides or bactericides. Essentially, these articles consist of polyamidic resins similar to those described in the cited U.S. Pat. No. 3,926,655. However, their molecular weight is higher, having a value of between 9,000 and 12,000. Its properties enable, according to patentees, the incorporation of a higher concentration of the active volatile substance, whose proportion can be as high as 70% of the weight of the resulting perfumed polymeric substrate.

The prior art refers also to processes intended to incorporate different additives, for example dyes or stabilizers, into granulated polymeric materials. This is known as the so-called "master-batch" technique which eminently consists in the preparation of concentrates of the dye or stabilizer into the matrices constituted by the same polymeric material, generally a polyolefin, than that used for the preparation of the end-product. Such a process has become widely accepted within the industry for its simplicity and efficiency [see in this respect: Rubber and Plastics, 42,3283 (1961)].

More recently, there have appeared on the market products with polyolefinic matrices suitable for "master-batch" processes. These are characterized by a high content of perfumed volatile substances. Eminently, they consist of a base of low density polyethylene (LDPE), of polypropylene and of ethylene vinyl acetate [see for example POLYIFF, registered trademark of INT. FLAVORS & FRAGRANCES, Inc.].

These polyolefinic concentrates are generally prepared by incorporating the perfume in suitable mixer at a temperature which varies as a function of the polymeric base. Polyethylene, for example, is treated at a temperature of between about 80° and 180° C. To the thus obtained viscous mass, the desired perfume is added before cooling and granulation. Such a process presents a major practical drawback inasmuch as the perfume incorporation occurs at high temperature with the consequent loss of a certain amount of volatiles and the modification of the constitution of the composition itself. This process therefore is of limited practical use.

The present invention offers a new solution to the problem set forth by the longlasting homogeneous diffusion of active volatile substances.

THE INVENTION

The present invention is based on the unexpected and unobvious observation that polyether-ester-amide type resins, known under the commercial name of PEBAX (registered trademark of ATO CHIMIE, Paris, France) absorb and diffuse afterwards advantageously volatile active substances. It has appeared that the shaped body of the invention offers the advantage of diffusing over a long period of time a uniform and sustained amount of the vapours of the active substance and consequently, it can find a utilization in various fields of applications such as the perfuming, odorizing or deodorizing of ambient air or closed spaces as well as in the field of insects control. The shaped body so obtained can be formed into useful objects of different aesthetical expressions, e.g. jewellery or decorative castings for decoration of apartments and offices. It can be fashioned easily by extrusion or moulding according to the techniques applied to shape thermoplastic polymeric materials. The typical features of the polyether-ester-amide used according to the invention are the following:

very extensive flexibility range
absence of plasticizers
excellent impact resistance
low variation of flexibility between $-40°$ and $+80°$ C.
excellent mechanical properties, and
good chemical resistance.

Its physical chemical properties are the following:

density: 1,01
melting point: 148° C.
tensile breaking point:
  a. constraint: 29 MPa
  b. elongation: 680%
hardness Shore: 75 A Owing to its properties, the shaped body of the invention can be employed either directly as a material to fashion volatiles emitting articles, or it can be used for the preparation of plastic concentrates having incorporated the active volatile substance, which concentrate can be used as additive to other thermoplastic resins in "master-batch" type processes. In this case, it is possible to incorporate easily a volatile active substance in concentrated form and as a solid to the mass of plastic material during the ordinary process of moulding or extrusion; no special equipment is required. The polyether-ester-amide resin used as a plastic base for the shaped body of the invention is compatible with various other thermoplastic resins, in particular with polyolefinic resins, EVA and PVC.

The shaped body of the invention can be used in conjunction with a variety of volatile active substances. When used to odorize, deodorize or perfume ambient air or enclosed spaces by emission of masking or fragrant vapour materials, e.g. vapours of a perfume oil, suitable active materials are selected from those perfume compounds or compositions generally used in the art to confer, enhance or modify the odorous properties of consumable materials.

The expert perfumer knows by experience that the nature of such compounds or compositions varies as a function of the odour effect it is desired to achieve, and that consequently it is here impossible to define all active operable materials. Specific examples are given in the specialized literature and, to this end, one can cite S. Arctander, "Perfume and Flavor Chemicals", Montclair, N.J. (1969).

The invention is better illustrated by, but not limited to, the following examples where the temperatures are indicated in degrees centigrade.

EXAMPLE 1

Perfuming of Polymer

150 Kg of polyether-ester-amide resin (PEBAX ®, 2533 SA OO; origin: ATO CHIMIE, Paris, France) in granulated form are introduced in a V form mixer and subjected to moderate stirring. Through a nozzle located in the mixer, 90 kg of a perfumed composition of floral type (origin: FIRMENICH SA, Geneva, Switzerland) are spra ed on the stirred granulates at room temperature. The perfume is thus absorbed by the plastic granulates which swell and become translucent. The mixing operation takes place in approximately ½ h; in such a manner, the perfume is completely absorbed in the mass of the granulates while leaving their surface completely dry. The optional addition of AEROSIL 200 (colloidal $SiO_2$; origin: DEGUSSA AG, West-Germany) at a concentration of 0.05% by weight can, if desired, improve the aspect of the surface by avoiding that it becomes sticky. The resulting perfumed granulates are used to perfume a thermoplastic polymeric base by the "master-batch" technique. The resulting product can be used to fashion perfumed articles of various form by moulding. It can be used also to manufacture plastic sheets that can be employed to the manufacture of active vapour diffusing membranes in plastic deodorizing articles (see for example French Patent No. 8201286).

EXAMPLE 2

Deodorizing Article for Dish-Washing Machines

An article destined to the use as a deodorizer for dish-washing machine was prepared as follows. In a V form mixer, 25 kg of PEBAX ® granulate (type 2533 SA OO prepared according to French Patent Application No. 2273021) were intimately mixed with 10 kg of polyethylenic resin (type HOSTALEN SV 1055, containing 35% by weight of polyvinylacetate) and 15 kg of a perfume base of lemon type. Stirring was kept during 1 h, which time was sufficient to complete the adsorption of the perfume oil into the polymeric mass. The perfumed base obtained can be used as an active adjuvant to perfume polyolefinic resins, for example low density polyethylene by the "master-batch" process. To this end, the perfumed polymeric base obtained as a granulate is mixed with the granulates of LD polyethylene at a concentration of 50 parts of perfumed base for 50 parts of polyethylene. The mixture obtained is extruded at a temperature of about 180°–220° C. The product obtained was used to fashion deodorizing articles by injection moulding at about 200°. The shaped articles under the form of a disc of a diameter of about 10–12 cm and a thickness of about 1 cm were used as perfuming element in the washing compartment of a dish-washing machine. Essays have shown that such an article enables the uniform, longlasting and controlled diffusion of the active vapours of the perfume oil during approximately 6 weeks.

EXAMPLE 3

Insecticide Article

By following the procedure described in Example 1 for the incorporation of the perfume oil into the polymeric mass, we have incorporated an active insecticide agent (DDVP, dimethyldichlorovinylphosphate) into the PEBAX polymeric mass. 30 Kg of DDVP, 25 kg of phenethylol and 25 kg of terpenes Portugal were mixed with 20 kg of PEBAX (type 2533 SN OO; origin: ATO CHIMIE). The resulting product was heated to 180°–200° and after homogenization, it was poured into appropriate moulds and cooled at room temperature. The resulting shaped articles diffuse into the environment the active insecticide vapours during several weeks without major retention of the active substance into the polymeric mass.

What we claim is:

1. A shaped volatiles emitting body consisting essentially of a thermoplastic polyamidic resin of polyether-ester-amide type of formula

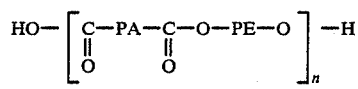

wherein PA represents the polyamide moiety and PE represents the polyether moiety, index n stands for an integer designating the multiple of the recurrent pattern, containing about 1 to 60% by weight, based on the total weight of the polyamidic resin, of a volatile substance selected from a perfume, an odorizer, a deodorizer, an insecticide, an insect- or an animal-repellent or attractant.

2. Shaped body according to claim 1 wherein PE in the polyether-ester-amide resin formula represents a linear or branched polyoxy-alkylene-aliphatic glycol wherein the alkylene radical has at least 2 carbon atoms.

3. Shaped body according to claim 2 wherein the polyether-ester-amide resin is obtained by reaction in the melting phase between a dicarboxylic polyamide having terminal carboxylic functions of a mean molecular weight of between about 300 and 15,000 and a linear or a branched aliphatic polyoxyalkylene glycol having terminal hydroxylic functions and of mean molecular weight of between about 200 and 6,000, said reaction being carried out under substantial reduced pressure and at temperatures of between about 100° and 400° C. in the presence of a catalyst consisting of a tetraalkyl-orthotitanate of general formula $Ti(OR)_4$, wherein R represents a linear or branched aliphatic hydrocarbon radical having a number of carbon atoms of between 1 and 24 and wherein its weight proportion with respect to the reaction mixture is of between 0.01 and 5%.

4. Article destined to odorize or deodorize ambient air or closed spaces substantially comprising the shaped volatiles emitting body of any of claims 1 to 3.

5. Article according to claim 4 wherein the closed space is the washing compartment of a dish-washing machine.

6. Article destined to repel, attract or kill insects substantially comprising as active element a shaped body according to any of claims 1 to 3.

* * * * *

UNITED STATES PATENT AND TRADEMARK OFFICE
CERTIFICATE OF CORRECTION

PATENT NO. : 4,734,278

DATED : March 29, 1988

INVENTOR(S) : Marc F. Pougalan and Gunter Holzner

It is certified that error appears in the above-identified patent and that said Letters Patent is hereby corrected as shown below:

On page 1, in the title, change "ESTERAMIDE" to -- ESTER-AMIDE --

On page 2, column 1, in the title, change "ESTERAMIDE" to -- ESTER-AMIDE --

Signed and Sealed this

Sixteenth Day of August, 1988

*Attest:*

DONALD J. QUIGG

*Attesting Officer*     *Commissioner of Patents and Trademarks*